United States Patent
Kurtz et al.

(10) Patent No.: US 6,820,753 B2
(45) Date of Patent: Nov. 23, 2004

(54) UNIVERSAL DISPOSABLE GLOVE DISPENSER BRACKET

(75) Inventors: Scotty R. Kurtz, Clarinda, IA (US); Marvin C. Negley, Clarinda, IA (US); Sandor Epstein, Marlboro, NJ (US)

(73) Assignee: Lisle Corporation, Clarinda, IA (US)

( * ) Notice: Subject to any disclaimer, the term of this patent is extended or adjusted under 35 U.S.C. 154(b) by 0 days.

(21) Appl. No.: 10/301,023

(22) Filed: Nov. 21, 2002

(65) Prior Publication Data

US 2004/0099623 A1 May 27, 2004

(51) Int. Cl.$^7$ .................................................. A47F 7/00
(52) U.S. Cl. ........................... 211/53; 211/49.1; 211/51; 211/59.2; 312/60; 312/121; 312/124
(58) Field of Search ................................ 211/85.17, 51, 211/50, 49.1, 59.2, 53; 248/905, 316.2, 316.7; 312/35, 60, 42, 121, 125

(56) References Cited

U.S. PATENT DOCUMENTS

| | | | | | |
|---|---|---|---|---|---|
| 3,089,597 | A | * | 5/1963 | Kaplan | 224/400 |
| 3,827,664 | A | * | 8/1974 | Larson | 248/905 |
| D250,240 | S | * | 11/1978 | Braginetz | D6/475 |
| D250,241 | S | * | 11/1978 | Braginetz | D6/475 |
| 5,865,413 | A | * | 2/1999 | Niemann et al. | 248/314 |
| 6,547,201 | B2 | * | 4/2003 | Barich et al. | 211/40 |
| 6,651,827 | B1 | * | 11/2003 | Eberwein et al. | 211/50 |
| 2003/0106867 | A1 | * | 6/2003 | Caterinacci | 211/40 |

OTHER PUBLICATIONS

McMaster–Carr Supply Co. Catalog 102, p. 785, 1996.

Printouts of Internet–access ads from various suppliers (7 pages).

* cited by examiner

Primary Examiner—Carl D. Friedman
Assistant Examiner—Jennifer E. Novosad
(74) Attorney, Agent, or Firm—Banner & Witcoff, Ltd.

(57) ABSTRACT

A disposable glove dispenser bracket includes a back panel with a magnetic pad attached thereto for supporting the dispenser and lateral side panels with flanges to grip and hold a glove dispenser box. A biasing spring maintains the glove dispenser box appropriately positioned within the dispenser bracket.

5 Claims, 2 Drawing Sheets

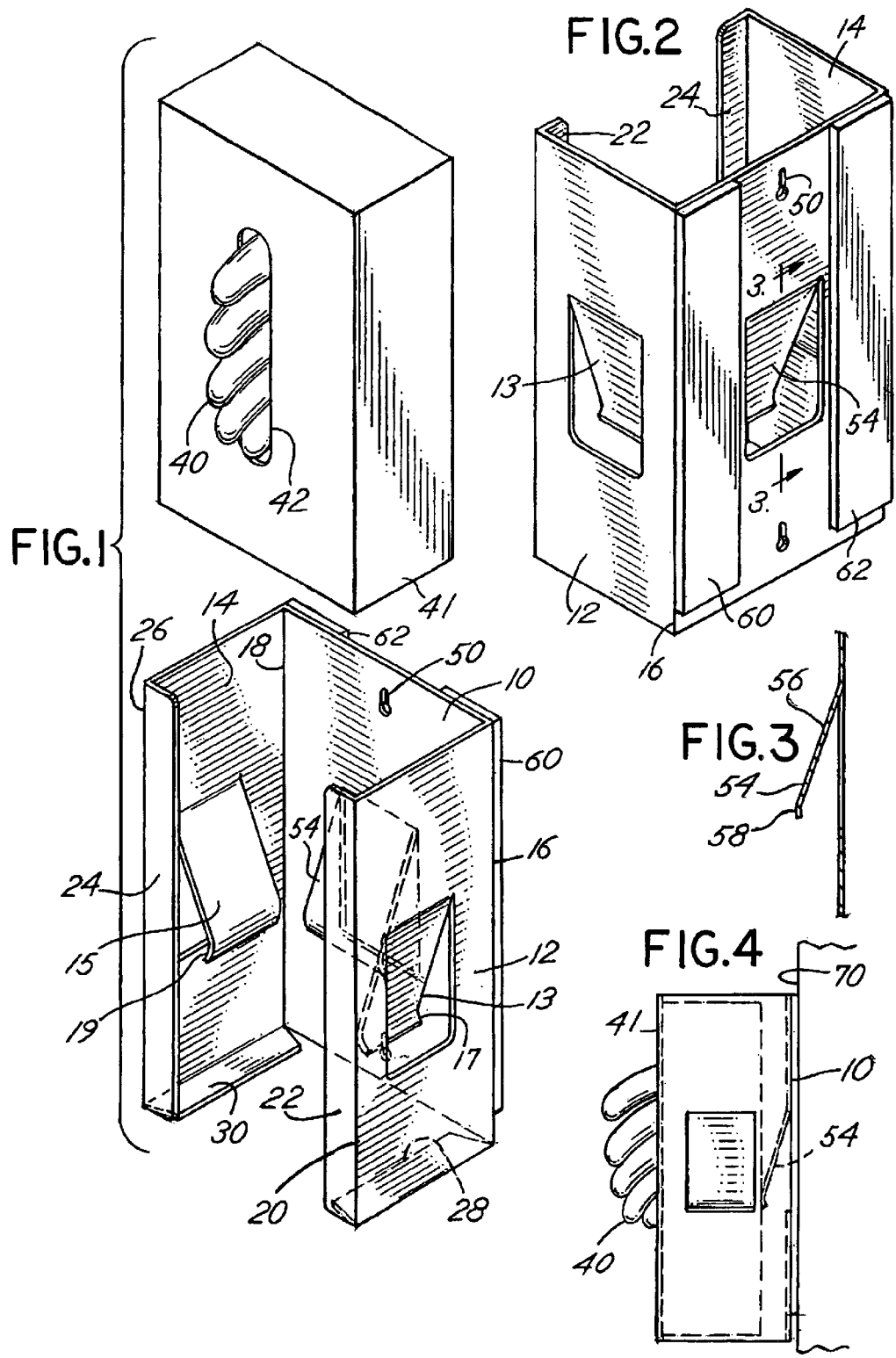

UNIVERSAL DISPOSABLE GLOVE DISPENSER BRACKET

BACKGROUND OF THE INVENTION

In a principal aspect, the present invention relates to a disposable glove dispenser bracket capable of holding and properly positioning boxed glove dispensers having a variety of sizes and shapes.

Food service workers, healthcare workers, and even garage mechanics often use disposable latex gloves when performing their various tasks. Such gloves protect against injury, dirt, and contamination. Typically such gloves come in cardboard carton packages with a removable, front side panel to facilitate dispensing of the gloves as needed. However, cardboard packages are easily misplaced, or may be relatively fragile and thus torn causing spoilage of the contents. Moreover, disposable glove packages or boxes are available, in various sizes and shapes, depending upon the manufacturer. Further, such glove dispenser boxes have access panels or tear away flaps having distinct configurations and positions with respect to the box construction. Consequently there has developed a need for a device which will safely and efficiently hold such boxes. Any such holder for disposable glove boxes, in order to be appropriately useful, must also have the capability of ease of mounting at an appropriate workstation or place in a work environment. These desires and features, among others, have led to the development of the present invention.

SUMMARY OF THE INVENTION

Briefly, the present invention comprises a disposable glove dispenser bracket for holding any one of a number of distinctly sized or shaped disposable glove containers or boxes. The dispenser bracket is comprised of a three-sided holder including a generally vertical, planar back side and first and second vertical, lateral sides extending outwardly and optionally converging from the back side. The dispenser is typically made from a metal such as steel or stainless steel. The lateral sides may converge toward each other and, because of the elastic metal construction, may provide a holding or biasing force on a box positioned between the sides. Preferably, the sides are parallel and each include an inwardly extending, integral biasing member or plate. Each of the lateral sides further includes front side and bottom side flanges to facilitate retention of a glove box by vertically supporting the box. The back side panel also preferably includes a biasing member integrally formed therewith. The back side biasing member is comprised of a generally integral, planar section of the back panel which is inclined forwardly from the back panel and includes an end tab or curved end construction which engages the disposable glove box and projects the box forwardly between the lateral sides. Similarly, the lateral sides each include integral, planar portions or sections which project inwardly toward each other to engage and hold a box. The outside face of the back side of the bracket includes multipole, magnetic members typically in the form of a pad or multiple pads affixed to the back side panel. The bracket may be made from stainless steel with the magnetic pad member affixed to the back side of the back panel. Alternatively, the back panel may be formed from a magnetic material to further enhance efficiency of the magnetic pad by providing a means for forming multiple magnetic loops or circuits through the back panel.

Thus it is an object of the invention to provide an improved disposable glove box dispenser holder or bracket.

It is a further object of the invention to provide a dispenser holder which can accommodate multiple sizes of boxes for gloves.

Another object of the invention is to provide a disposable glove box holder that is economical, easily movable from site to site as needed, will accommodate multiple sizes of disposable glove storage boxes, will accommodate glove boxes having multiple access panels and access panel positions, and which is rugged.

These and other objects, advantages, and features of the invention will be set forth in the detailed description which follows.

BRIEF DESCRIPTION OF THE DRAWING

In the detailed description which follows where reference will be made to the drawing comprised of the following figures:

FIG. 1 is an isometric view of a first embodiment of the disposable glove dispenser package holder of the invention depicting the manner in which a disposable box may be retained.

FIG. 2 is an isometric view of the back side construction of the disposable glove dispenser package holder of FIG. 1;

FIG. 3 is a cross sectional view of the back side of the holder of FIG. 2 taken substantially along the line of 3—3;

FIG. 4 is a side elevation of the holder of FIG. 1 shown attached to a magnetizable surface with a disposable glove box retained therein.

DESCRIPTION OF THE PREFERRED EMBODIMENT

Figure 5:
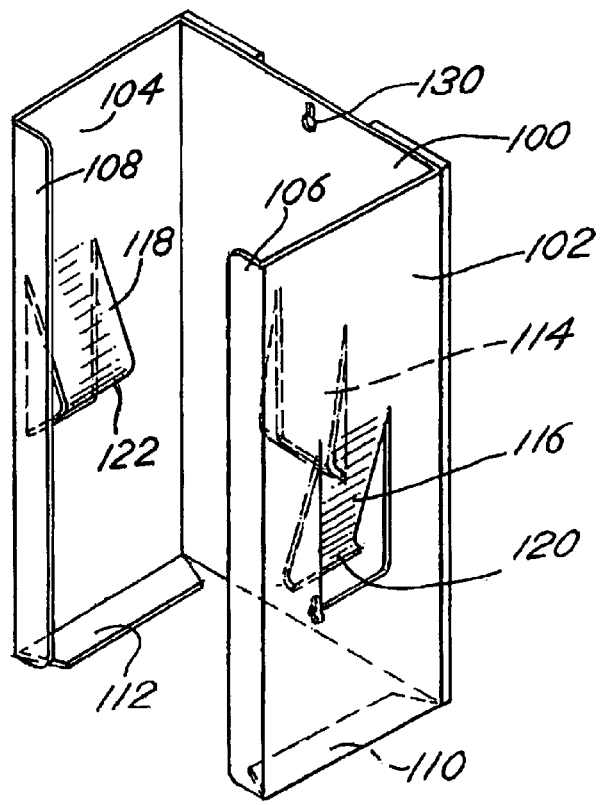
FIG. 5 is an isometric view of a second preferred embodiment of the invention viewed from the front side of the device.

Referring to FIGS. 1–4, a first embodiment of the disposable glove dispenser bracket or holder of the invention is comprised of a shaped metal bracket having a back panel or side 10, a first lateral side 12, and a second lateral side 14. The back panel or side 10 has a generally rectangular shape as do the first and second lateral sides 12 and 14. The first lateral side 12 joins to the back side or panel 10 along a boundary or edge 16. In a similar manner, the second lateral side 14 joins to the back panel or side 10 along a boundary or edge 18. In practice, the dispenser bracket is formed from sheet metal such as stainless steel sheet or steel sheet, and is shaped by bending along the boundaries or edges 16 and 18. Thus a rectangular plate of sheet metal may be stamped and formed as depicted in the figures. A preferred steel is described as ¼ hard steel which has the feature of an appropriate spring characteristic, which enables the formed dispenser to be altered in shape by bending but still exhibit spring forces on a glove container placed in the dispenser.

The first lateral side 12 includes a front edge 20 with a flange 22. The front edge flange 22 extends inwardly toward a coplanar flange 24 on the front edge or boundary 26 of the second lateral side 14. The lateral sides or panels 12 and 14 are thus generally identical in shape and size and therefore generally congruent one with respect to the other. The first side 12 further includes a bottom edge support flange 28. The second lateral side 14 also includes a bottom edge support flange 30. The flanges 28 and 30 are coplanar and project toward one another.

Figure 6:
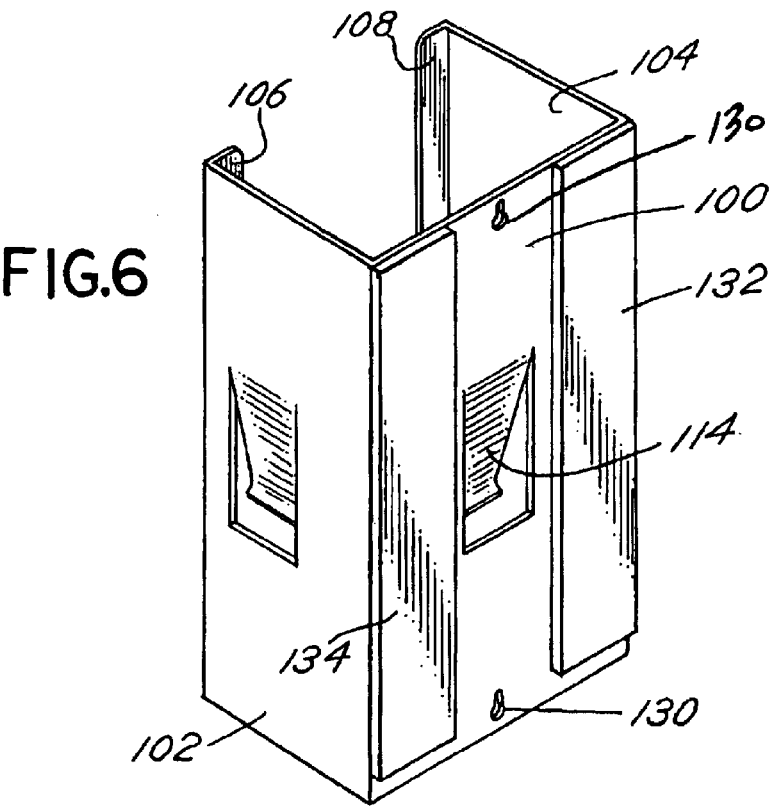
FIG. 6 is an isometric view of the holder of FIG. 5 viewed from the back side.

The lateral sides at 12 and 14 are each formed with an inwardly extending spring or biasing member 13, 15. Spring members 13, 15 extend downwardly and inwardly from the plane of sides 12, 14 toward each other so that they can easily engage against a box 41 in the bracket. Alternatively, as depicted in FIGS. 5 and 6, the lateral sides 12 and 14 may converge slightly toward one another to grip or grasp a box 41 of disposable gloves 40 fitted in the dispenser bracket. The angle of convergence is in the range of about 5° to 20°.

The flanges 22, 24, 28, and 30 support a dispenser box 41 and preclude a box 41 from falling downwardly out of the bracket or from being forced forwardly from the bracket. The spring members 13, 15 or converging side walls 12 and 14 facilitate maintaining the box 41 snuggly therebetween. Because the flanges 22 and 24 are spaced one from the other, a dispensing opening 42 in the box 41 is exposed when the box 41 is placed within the dispenser bracket.

The dispenser bracket further includes one or more keyed openings 50 through the back panel 10 in order to suspend the bracket from a hangar. The back panel or side 10 further includes an inclined biasing or spring member 54 in the form of an inclined planar member which is formed by stamping and bending the planar member 54 inwardly from the plane of the back panel 10 causing it to extend downwardly and forwardly as depicted in the figures. The planar member 54 includes a first depending inclined section 56 (FIG. 3) extending from approximately the midpoint of the back panel 10 downwardly and forwardly or inwardly and in alignment with spring members 13, 15. Importantly, the inclined panel 54 further includes a tab or terminating section 58 (FIG. 3) at its free end which is curved or shaped in a manner which will facilitate positioning thereof against the back side of the box 41 to thereby force the box 41 toward the flanges 22 and 24. The curved end 58 also allows the empty box to be easily inserted and removed from the bracket. Side spring members 13, 15 have similar curved sections 17, 19. Preferably the tab end 58 of member 54 is arcuate in shape and extends generally laterally between the first and second side panels 12 and 14. The inclined planar member 54, as do spring members 13, 15, thus provide a biasing means for engaging, guiding and holding the dispenser box 41. Thereby the dispenser bracket accommodates boxes 41 of multiple sizes, shapes, and capacity. Of course it is possible merely to use one planar biasing or spring member 13 or 15 and adjust the size of the flanges 22, 24, 28 and 30. The side panels or lateral sides 12 and 14 extend at preferably right angles from the back panel 100 in the embodiment of FIGS. 1–4.

Thus, in the embodiment, three inwardly projecting planar portions or biasing members 13, 15, 54 all extend inwardly and downwardly to approximately the mid-point between the top and the bottom edge of the holder. These planar portions 13, 15 and 54 serve to center or position a dispenser box 41 between the front edge flanges 22, 24, thus making access to the contents of the box 41 improved. Note that the back panel 10 may include a keyed opening 50 and a bottom slot 51 for attaching the holder to a wall in lieu of using the magnetic pads 60 and 62. Note also that the planar spring members 13, 15, 54 extend inwardly and downwardly from the respective sides 12, 14, 10. They may however extend upwardly or may be arrayed in a pattern or multiple spring members in the form of fingers may be provided. For example the back side biasing member 54 may extend outwardly and downwardly whereas lateral side biasing members 13 and 15 may extend upwardly and inwardly. Variations of the construction are possible to enhance the universality of the device.

A magnetic, multipole pad or pads 60 and 62 are affixed to the outside of the back panel 10. The pad or pads 60 and 62 are fixed vertically across the entire back side of the panel 10 in one preferred embodiment and in a further preferred embodiment may cover the entire back side. A typical pad material is provided by Polymag, Inc., product no. PM8 with PSA (Pressure Sensitive Adhesive). It is a multipole pad which, in combination with a magnetizable back panel 10, and a magnetizable mounting surface, such as surface 70 shown in FIG. 4, provides a series of magnetic circuits that will facilitate support of the dispenser bracket and dispenser box 41 on a surface. The pads 60 and 62 are typically attached to the back panel 10 by means of an adhesive. Magnetic forces then attach the bracket to a magnetizable surface 70 such as a tool locker and maintain the dispenser and box 41 on that surface 70. Of course, the dispenser bracket and its contents may be moved by breaking the magnetic contact with the support surface 70.

FIGS. 5 and 6 illustrate a second preferred embodiment. In the second embodiment of FIGS. 5 and 6, a back panel 100 is joined to a first side panel 102 and to a second side panel 104 with forward or front side flanges 106 and 108 extending from the side panels 102 and 104, respectively. The first and second lateral sides 102 and 104 include inwardly projecting, coplanar bottom edge flanges 110, 112 respectively. Back panel 100 includes a forwardly extending planar biasing spring member or section or planar portion 114, substantially in the form and size described with respect to the first embodiment. With the second embodiment, however, each or at least one of the lateral sides 102 and 104 is converging. The inwardly converging sides 102 and 104 act as elastic or biasing members and facilitate engaging and positioning a glove dispenser box retained within the bracket.

The back panel 100 preferably includes openings or slots 130 for hanging the dispenser on a hook or hanger in a wall surface, for example. Preferably, magnetic pads 132 and 134 are provided on the backside of the back panel 100. In the embodiment depicted, the magnetic pads 132, 134 comprise first and second vertically, spaced parallel pads 132, 134 positioned on the back panel positioned opposite sides of the forwardly biasing panel member 114. The embodiment of FIGS. 5 and 6 preferably includes side panel biasing members 116 and 118 having shaped or arcuate box engaging ends 120 and 122 respectively. Thus, biasing a glove box may be effected by the combination of converging sides 102, 104 as well as spring members 114, 116 and 118.

Various other alternatives may be incorporated into the design of the invention. The lateral sides 12 and 14 may be discontinuous. The shape and arrangement of the magnetic pads on the back side of panel 10 or 100 may be significantly altered. The number and extent of the spring biasing planar members 13, 15, 54 (114, 116, 118) may be varied. The inward extent and configuration of the flanges 28, 30, 22 and 24 may be varied. The material utilized to make the dispenser bracket may be varied, though a magnetizable back panel 10 is preferred. The preferred material is, as previously disclosed, a ¼ hard steel which permits the side panels, e.g. 102, 104 to be bent to form different angles with respect to the back panel 100, i.e. diverging, right angles, or converging, thereby accommodating in a gross adjustment sense, a glove box depending upon the size of the box. The spring characteristics of the material coupled with or without the spring members, e.g. 114, 116, 118, then provide a holding force customized for the glove box held in the dispenser. The dispenser can therefore be adjusted to match the size and shape of the glove box 41. Thus, numerous variations and combinations are considered to be within the scope of the invention and the invention is limited only by the following claims and equivalents thereof.

What is claimed is:

1. A disposable glove dispenser bracket for holding any one of a number of disposable glove containers comprising, in combination:

a three sided elongate channel including a back side, a first lateral side and a second lateral side spaced from the first lateral side, said first and second lateral sides joined respectively to the back side along first and second parallel, connection boundaries, said first and second lateral sides being generally congruent in size and shape and extending outwardly from the back side and generally parallel to one another, said sides defining an open top;

said lateral sides each terminating at a front edge, each lateral side including a lower edge;

a retention flange at each front and each lower edge of each lateral side, each retention flange extending inwardly toward one another, said retention flanges being spaced from one another, said lateral side lower edge retention flanges comprising spaced container support members, said lateral side front edge retention flanges comprising spaced container retention members;

a separate biasing member formed integrally in the back side and in each of said lateral sides, each of said biasing members extending toward the region between the back and the lateral sides, said biasing members in the form of an inclined planar member with an end tab extending laterally between the sides and downwardly from the open ton whereby a glove container with an open front can be inserted downwardly into the dispenser bracket between the lateral sides and retained by the biasing member end tabs and the retention flanges.

2. The dispenser bracket of claim 1 further including a magnetic member mounted on the back side to attach the dispenser bracket onto a magnetizable material surface.

3. The dispenser bracket of claim 1 wherein the biasing member end tabs substantially align with each other for engagement with a box.

4. The dispenser bracket of claim 1 formed from a sheet of steel material.

5. The dispenser bracket of claim 1 including first and second generally parallel magnetic pads affixed on opposite sides of the back side biasing member.

* * * * *